(12) United States Patent
Nguyen

(10) Patent No.: US 9,517,131 B2
(45) Date of Patent: Dec. 13, 2016

(54) CARDIAC VALVE REPAIR DEVICE

(71) Applicant: Than Nguyen, Huntington Beach, CA (US)

(72) Inventor: Than Nguyen, Huntington Beach, CA (US)

( * ) Notice: Subject to any disclaimer, the term of this patent is extended or adjusted under 35 U.S.C. 154(b) by 34 days.

(21) Appl. No.: 14/724,424

(22) Filed: May 28, 2015

(65) Prior Publication Data

US 2016/0166382 A1 Jun. 16, 2016

Related U.S. Application Data

(63) Continuation-in-part of application No. 14/569,385, filed on Dec. 12, 2014, now abandoned.

(51) Int. Cl.
*A61F 2/24* (2006.01)

(52) U.S. Cl.
CPC .............. *A61F 2/246* (2013.01); *A61F 2/2454* (2013.01); *A61F 2/2412* (2013.01); *A61F 2230/0008* (2013.01); *A61F 2230/0054* (2013.01); *A61F 2230/0056* (2013.01)

(58) Field of Classification Search
CPC .......... A61F 2/246; A61F 2/2454; A61F 2/24; A61F 2/2418; A61F 2/2412
See application file for complete search history.

(56) References Cited

U.S. PATENT DOCUMENTS

| | | | |
|---|---|---|---|
| 7,704,277 B2 | 4/2010 | Zakay et al. | |
| 8,449,599 B2 * | 5/2013 | Chau | A61F 2/2418 623/1.24 |
| 8,460,370 B2 | 6/2013 | Zakay et al. | |
| 8,870,948 B1 * | 10/2014 | Erzberger | A61F 2/2412 623/2.1 |
| 2004/0260393 A1 | 12/2004 | Rahdert et al. | |
| 2008/0140190 A1 | 6/2008 | Macoviak et al. | |
| 2008/0319541 A1 | 12/2008 | Filsoufi | |
| 2009/0005863 A1 * | 1/2009 | Goetz | A61F 2/2418 623/2.18 |
| 2010/0280606 A1 | 11/2010 | Naor | |
| 2012/0323313 A1 | 12/2012 | Seguin | |
| 2013/0282110 A1 * | 10/2013 | Schweich, Jr. | A61F 2/243 623/2.11 |
| 2014/0005778 A1 | 1/2014 | Buchbinder et al. | |
| 2014/0067048 A1 * | 3/2014 | Chau | A61F 2/246 623/2.1 |

* cited by examiner

*Primary Examiner* — Jason-Dennis Stewart
(74) *Attorney, Agent, or Firm* — Raymond Sun

(57) ABSTRACT

A cardiac valve repair device has a membrane assembly and a frame. The frame has a central structure that defines a central separation, a pair of sleeves positioned below the central structure, and a pair of atrial alignment expansion beams. Each atrial alignment expansion beam has a curved section and inner section at each opposite end that defines a scissor-crossing where they overlap each other to form a separate lower expansion clip beam at each of the opposite ends thereof. The cardiac valve repair device also includes a pair of upper expansion clip beams. A V-shaped ventricular expansion curved beam extends below the two sleeves, with the membrane assembly secured to the V-shaped ventricular expansion curved beam. A pair of ventricular alignment stabilizing beams extends downwardly from the two sleeves.

6 Claims, 14 Drawing Sheets

CARDIAC VALVE REPAIR DEVICE

RELATED CASES

This is a continuation-in-part of Ser. No. 14/569,385, filed Dec. 12, 2014, and claims priority from 61/915,091, filed Dec. 12, 2013, both of whose disclosures are incorporated by this reference as though set forth fully herein.

BACKGROUND OF THE INVENTION

1. Field of the Invention

The present invention generally relates to apparatus and methods for performing surgical, transcatheter or minimally invasive repair of a defective cardiac valve, such as the mitral, aortic, tricuspid and pulmonary valves.

2. Description of the Prior Art

The human heart has four major valves which moderate and direct blood flow in the cardiovascular system. These valves assure a unidirectional flow of blood supply through the cardiovascular system. Whereas the aortic, pulmonary, and tricuspid valves have three leaflets, the mitral valve has only two leaflets. The mitral valve and aortic valve control the unidirectional flow of oxygen-rich blood from the lungs to the body. The mitral and aortic valves direct the oxygen-rich blood received from the lungs into the systemic circulation under the pumping action of the left ventricle. The tricuspid and pulmonary valves ensure unidirectional flow of oxygen-depleted blood received from the right atrium towards the lungs by the pumping action of the right ventricle.

Heart valves are passive structures composed of leaflets that open and close in response to differential pressures on either side of the valve. As an example, oxygen-rich blood flows from the lungs into the left atrium. When the left ventricle expands, the low pressure under the mitral valve allows it to open for blood flow from the left atrium to the left ventricle. When the ventricle contracts to pump blood out to the body, a high pressure is created under the mitral valve, closing it to prevent blood from leaking back toward the atrium into the lungs.

Congenital, inflammatory, infectious conditions or diseases may lead to dysfunction of the valves over time. Such degradation may result in serious cardiovascular compromise or even death. The mitral valve and the aortic valve which are subjected to the systemic circulation high pressure generated by the left ventricle are more susceptible to dysfunction, such as stenosis or regurgitation.

For example, a stenotic mitral valve may impede blood flow into the heart, causing blood to back up and pressure to build in the lungs. Regurgitation occurs when the mitral valve leaflets do not coapt correctly, thus causing blood to leak backwards into the left atrium and lungs each time the heart pumps. Improper coaptation of the mitral valve leaflets thus requires the heart to pump more blood with each contraction to eject the necessary amount of blood for systemic circulation; a process called volume overload. Although the heart may gradually compensate for this overload as the leakage progresses slowly through months and years, the heart will eventually begin to fail.

Medical treatments to address dysfunctional valves involve either repairing the diseased native valve or replacing it with mechanical or biological valve prosthesis. All current valve prostheses have disadvantages, such as need for long-term maintenance with blood thinners, the risk of clot formation, limited durability, etc. Valve repair, due to its short term use of blood thinner and low risk of thrombosis, is preferable to valve replacement when possible. Today, standard valve replacement or repair procedure still requires an open-heart surgery which is prone to many complications and long hospital stays for recuperation.

Percutaneous techniques have been developed recently for less invasive implantation of a replacement valve without the need for open-heart surgery. In such techniques, the replacement valve is crimped to a small profile compatible to the blood vessel lumen size, and then mounted to the end of a flexible catheter. It is then advanced through the blood vessel of a patient until the prosthetic valve reaches the implantation site. The valve is then deployed to its functional size at the site of the defective native valve. The expansion of the valve to its normal size could be through self-expansion or by balloon expansion. The expanded prosthetic valve pushes the native valve leaflets aside and renders them ineffective. Examples of such devices and techniques, wherein the native valve is replaced in its entirety by a substitute tissue valve, are described, for example, in U.S. Pat. Nos. 6,582,462 and 6,168,614 to Andersen et al.

With the success of percutaneous valve replacement in the aortic position, catheter-based mitral valve replacement and repair techniques for correcting mitral regurgitation have been pursued. Several technologies have been developed ranging from iterations of the Alfieri stitch procedure, to coronary sinus-based modifications of mitral anatomy, to subvalvular placations, or ventricular remodeling devices.

Mitral valve regurgitation often arises due to mitral annulus dilatation, which may be treated using a surgical technique to narrow and restore the natural shape the annulus. Prosthetic annuloplasty rings are therefore an important addition to mitral valve repair techniques. A primary role of the annuloplasty ring is to reduce the size of the annulus and decrease the tension on the sutures while providing flexibility and mobility at the same time.

One recent technique for correcting mitral valve leakage is described in U.S. Pat. No. 6,269,819 to Oz et al., which employs a percutaneously introduced clipping apparatus into a leaking mitral valve. Once positioned, the clip arms are activated to hold a short segment of the coaptation edges of both the anterior and posterior leaflets together to reduce mitral regurgitation. Because the clip transforms the mitral orifice into two orifices, the clip may significantly obstruct the flow of blood through the valve.

The native structures of the mitral valve apparatus (mitral annulus and leaflets, chordae, papillary muscles, etc.) play an important role in left-ventricular function and therefore any valve replacement system that does not respect these elements may adversely impact the left-ventricular function. Current trans-catheter mitral valve replacement in development requires anchoring the device to the annulus and leaflets of the native valve. This immobilizes the native leaflets, exerts tension to the chordae, and impairs the native function of the annulus, which can result in left-ventricular outflow tract (LVOT) obstruction and systolic anterior motion (SAM), etc.

In view of the above-noted drawbacks of previously-known systems, it would be desirable to provide a device, and methods of using the same, that assists the functioning of the native cardiac valve, rather than removing or entirely supplanting the native valve. It would also be desirable to provide a device having prosthetic leaflets, and methods of using the same, that reduce tension on the prosthetic leaflets, thereby increasing the life of the prosthesis. It would be further desirable to provide a device having a support frame, and methods of using the same, wherein the prosthesis is configured to self-align with the native valve annulus when deployed, without deformation. It would also be desirable to provide a device, and methods of using the same, that may be deployed with reduced risk of obstructing blood flow relative to previously known mitral valve repair techniques.

SUMMARY OF THE DISCLOSURE

In addition to the objects set forth above, the present invention provides a cardiac valve repair device that can be suspended within the flow path of a defective cardiac valve to reduce the prolapsed segment of the native valve leaflets, while retaining much of the native valve's structure and function.

The present invention provides a cardiac valve repair device having a membrane assembly and a frame. The frame has a central structure that defines a central separation, a pair of sleeves positioned below the central structure, and a pair of atrial alignment expansion beams. Each atrial alignment expansion beam has a curved outer flange section that together defines a generally oval shape, each opposite end of the flange section having a curved section that transitions into an inner section that extends radially towards the middle of the combined flange sections. The combined curved section and inner section of the two atrial alignment expansion beams at each opposite end define a scissor-crossing where they overlap each other to form a separate lower expansion clip beam at each of the opposite ends thereof. The cardiac valve repair device also includes a pair of upper expansion clip beams, each having an M-shaped wing section that includes at least one wing tip, each wing section having two legs that converge downwards towards one of the sleeves, with one leg transitioning to a part of a central structure. A V-shaped ventricular expansion curved beam extends below the two sleeves, with the membrane assembly secured to the V-shaped ventricular expansion curved beam. A pair of ventricular alignment stabilizing beams extends downwardly from the two sleeves.

Exemplary embodiments of the inventive prosthetic frame and membranes assembly include an expandable frame and one or more prosthetic membranes coupled to the frame. The expandable frame may be configured to transition from a contracted delivery state to an expanded deployed state. Advantageously, the cardiac valve repair device of the present invention is configured such that one or more prosthetic membranes are suspended just above the coaptation of the native leaflets to further limit the upward travel, in particular the prolapsed segment, thereby improving functioning of the native valve.

In accordance with one aspect of the invention, the cardiac valve repair device may be compressed and loaded on to a conventional delivery catheter and delivered to the mitral position using a transvascular approach according to techniques known in the art.

The frame for the cardiac valve repair device may comprise a metal alloy (e.g., nickel-titanium), or a polymer frame covered by animal tissue or synthetic fabric.

In accordance with another aspect of the present invention, an exemplary catheter is provided for delivering the cardiac valve repair device transvascularly, transseptumly or transapically to the location of a defective cardiac valve. The catheter may include a main body with multiple tubular structures which can be independently activated to sequentially deploy different members of the cardiac valve repair device. Sutures or wire guides attached to the cardiac valve repair device are threaded through the tubes to load, unload and retrieve the cardiac valve repair device to the catheter.

BRIEF DESCRIPTION OF THE DRAWINGS

FIG. 1b is a perspective view of the frame assembly of the cardiac valve repair device of FIG. 1a.

FIGS. 2a and 2b illustrate the atrial alignment expansion beams of the cardiac valve repair device of FIG. 1a.

FIG. 3 illustrates the upper expansion clip beams of the cardiac valve repair device of FIG. 1a.

FIG. 4 illustrates the central structural beams of the cardiac valve repair device of FIG. 1a.

FIG. 5 illustrates the lower expansion clip beams of the cardiac valve repair device of FIG. 1a.

FIG. 6 illustrates the ventricular expansion curved beam of the cardiac valve repair device of FIG. 1a.

FIG. 7 illustrates the ventricular alignment stabilizing beams of the cardiac valve repair device of FIG. 1a.

FIG. 8 illustrates the membrane assembly of the cardiac valve repair device of FIG. 1a.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of the invention. The scope of the invention is best defined by the appended claims.

Figure 1A:
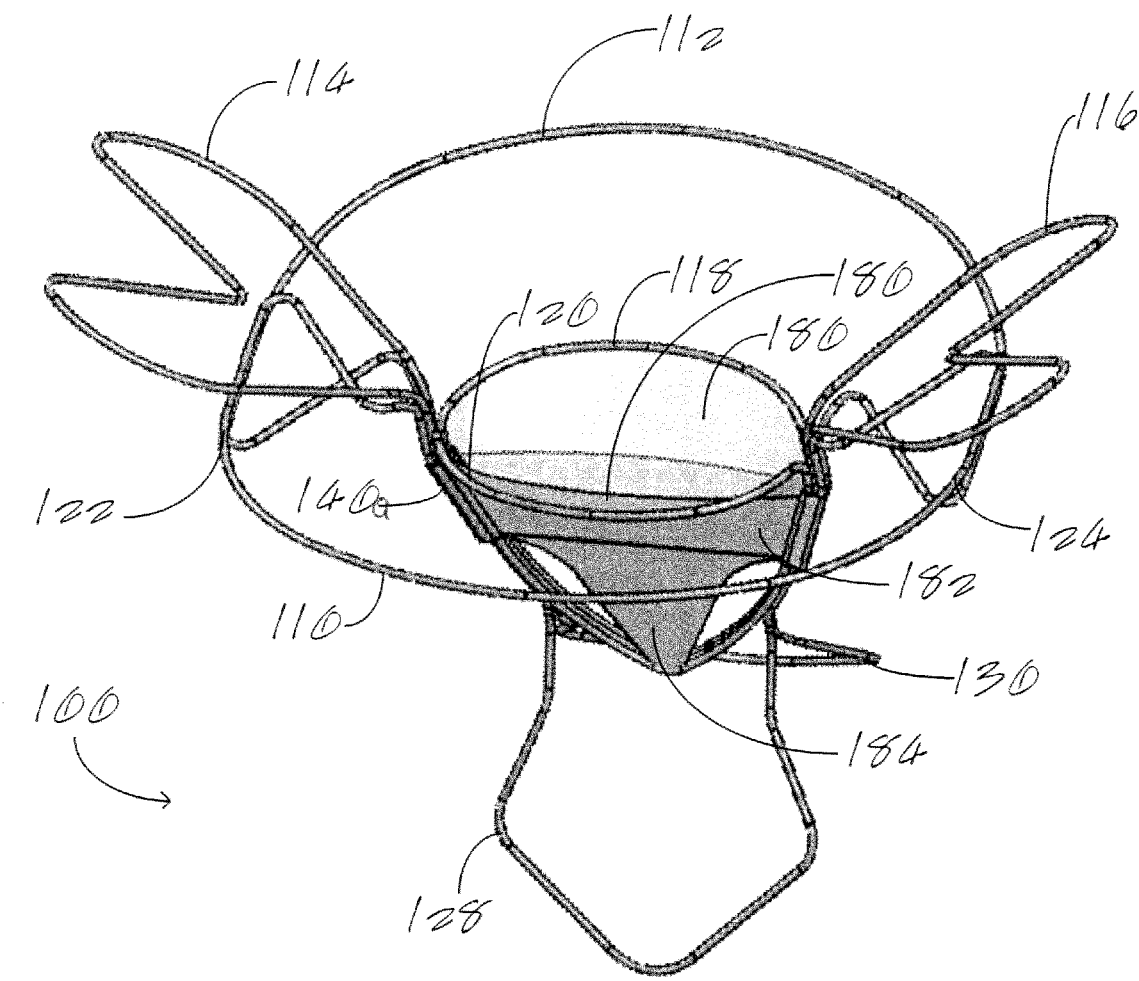
FIG. 1a is a perspective view of a cardiac valve repair device according to a first embodiment of the present invention.
Figure 1B:
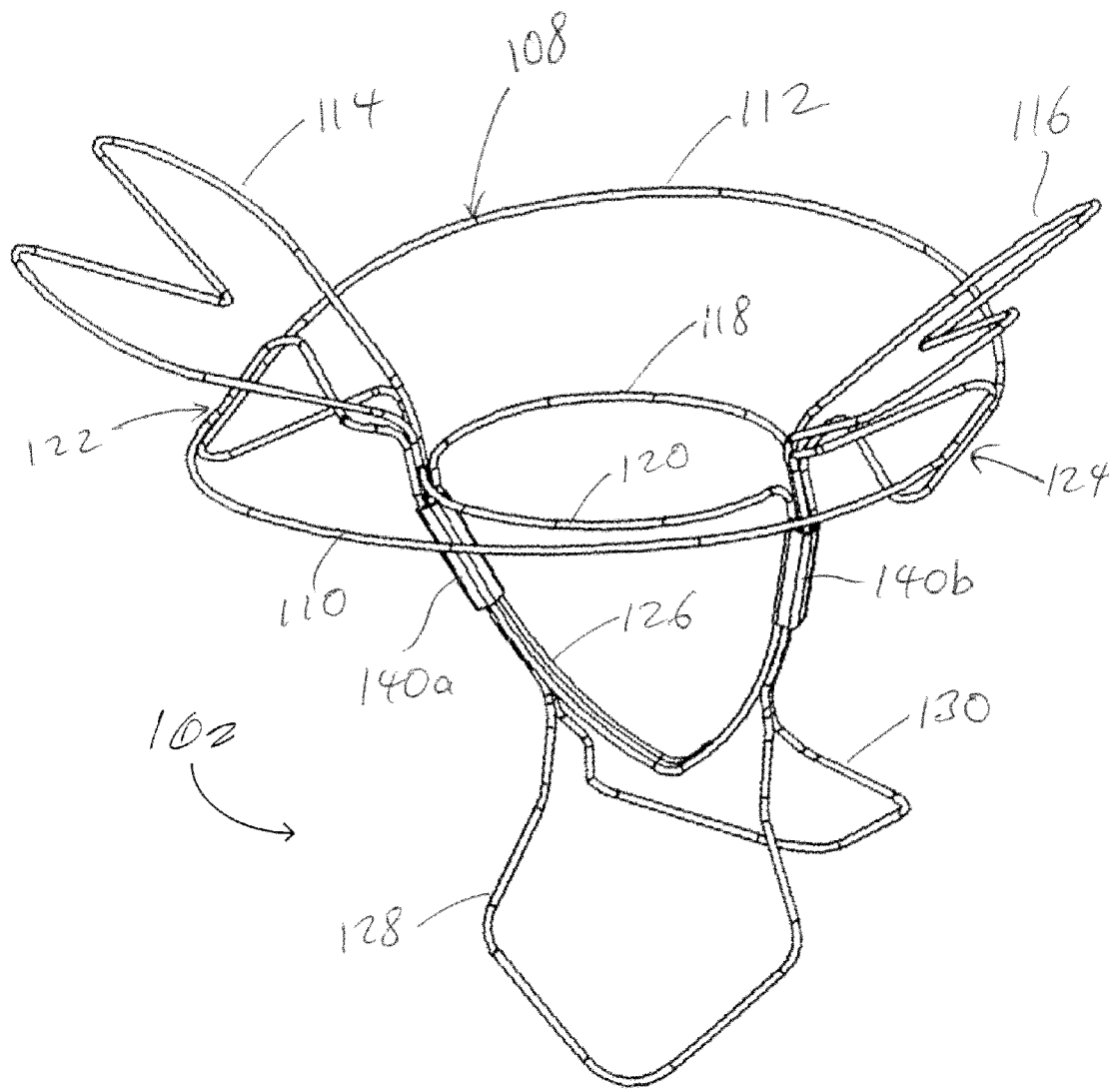

As shown in FIGS. 1a and 1b, the cardiac valve repair device 100 of the present invention has the following two main structural components: a support frame assembly 102 and a membrane assembly 104. The membrane assembly 104 comprises a plurality of membranes which can be constructed from either synthetic material (e.g., PTFE) or biological material (e.g., pericardium). They serve as outer covering membranes positioned above the native mitral valve's anterior and posterior leaflets, and function to prevent mitral valve leaflet prolapse. They come into contact with the native mitral valve leaflet's free margin and leaflet surface, both of which form the valve's coaptation surfaces.

The support frame assembly 102 is made up of a wire frame 108 that can be manufactured from a shape memory material (e.g., Nitinol™) which serves to attach and position the membranes above the native mitral valve. The frame 108 aligns in a non-anchored self-aligning manner, positioning the device 100 along the commissure-commissure axis above and between the anterior and posterior leaflets of the native mitral valves, and allowing motion of the frame 108 along the native valve's axial/radial motion.

Figure 2A:
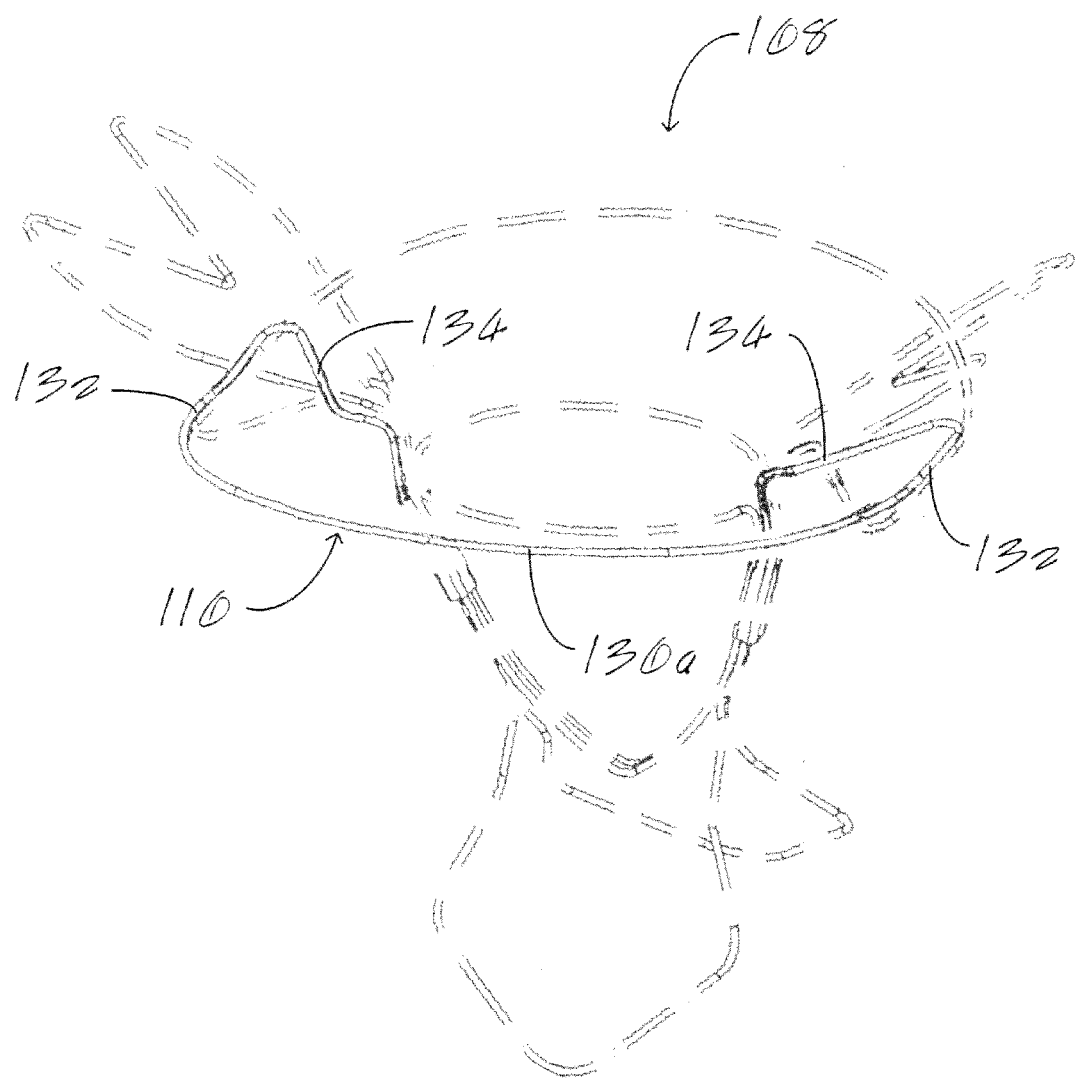
Figure 2B:
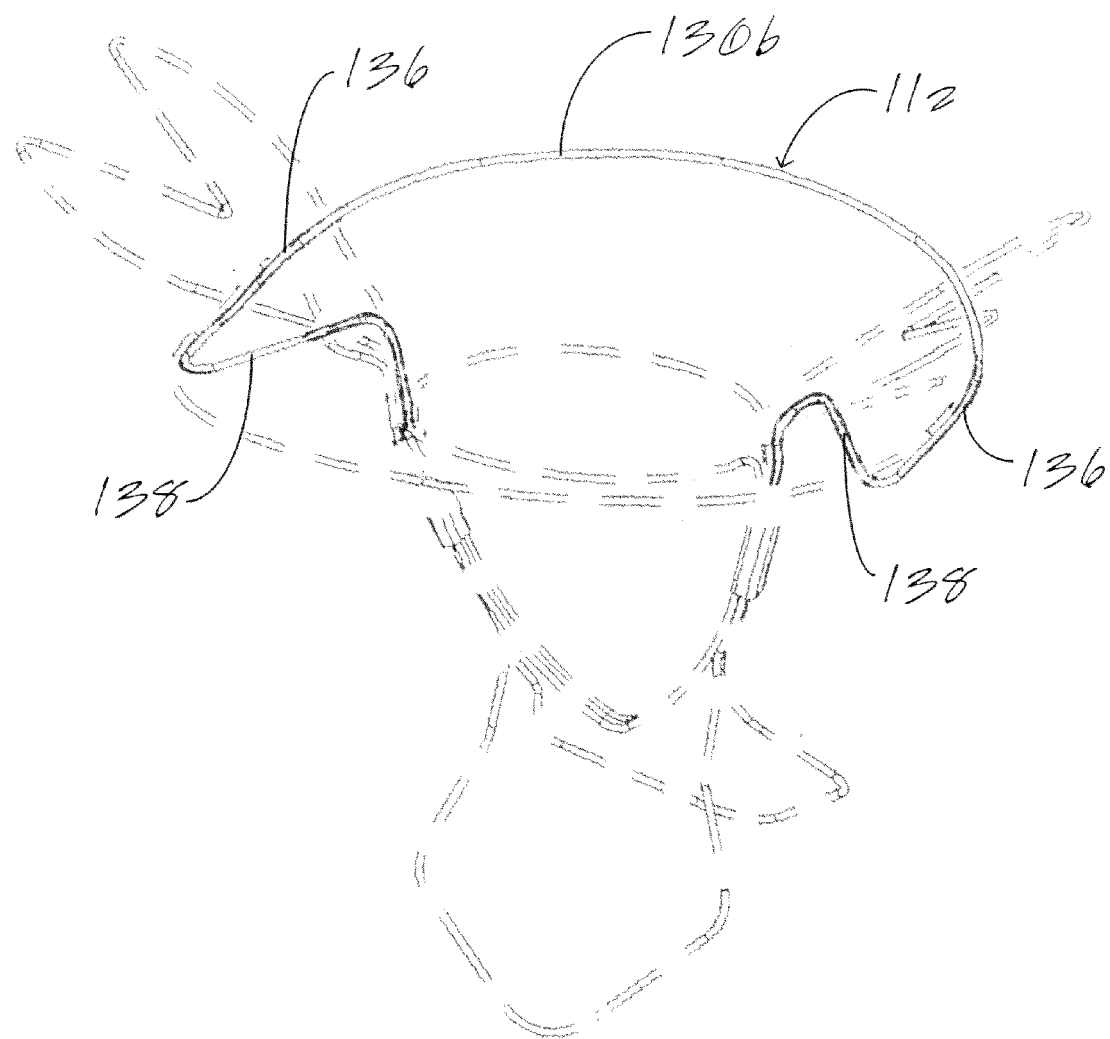
Figure 3:
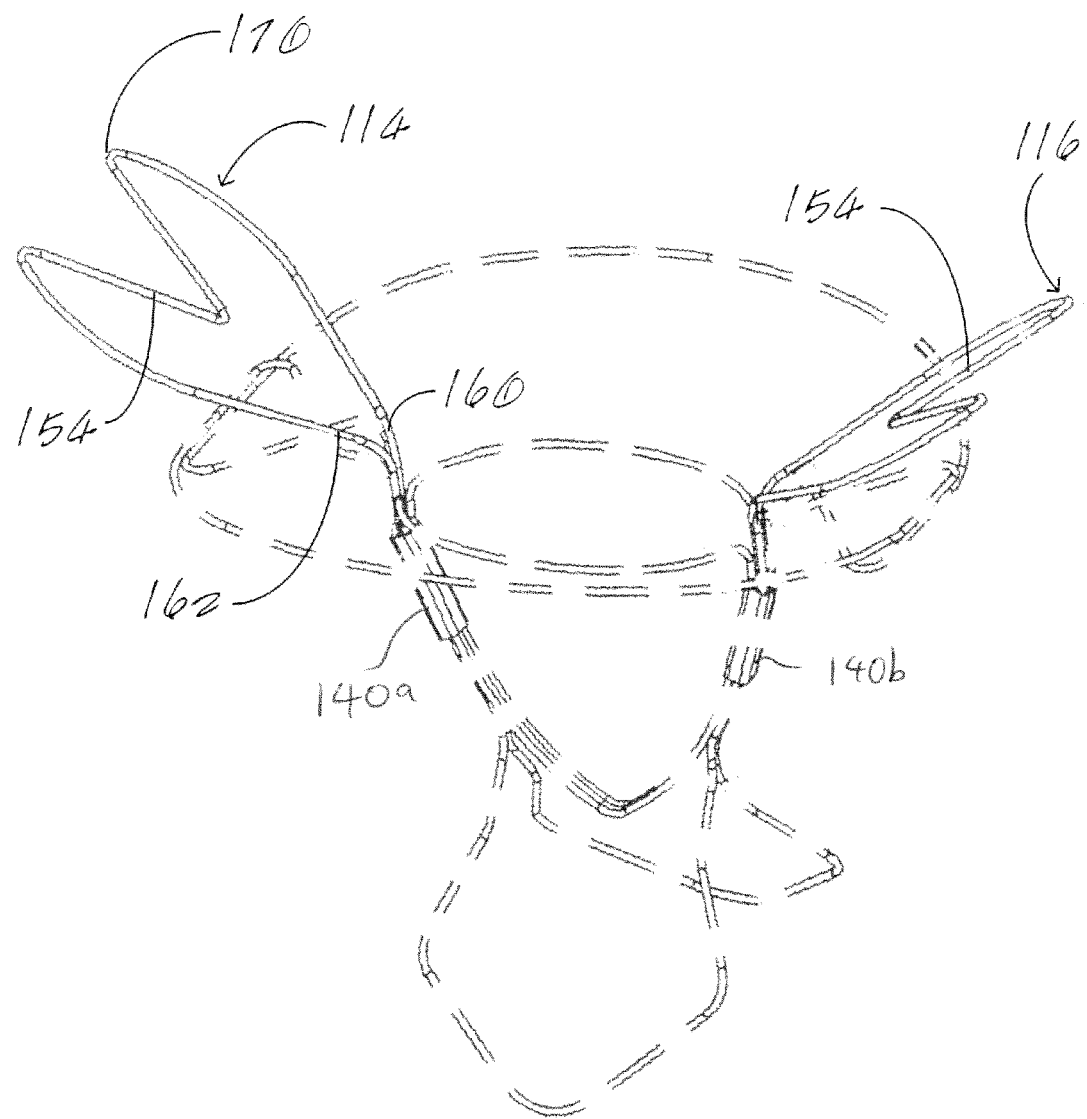
Figure 4:
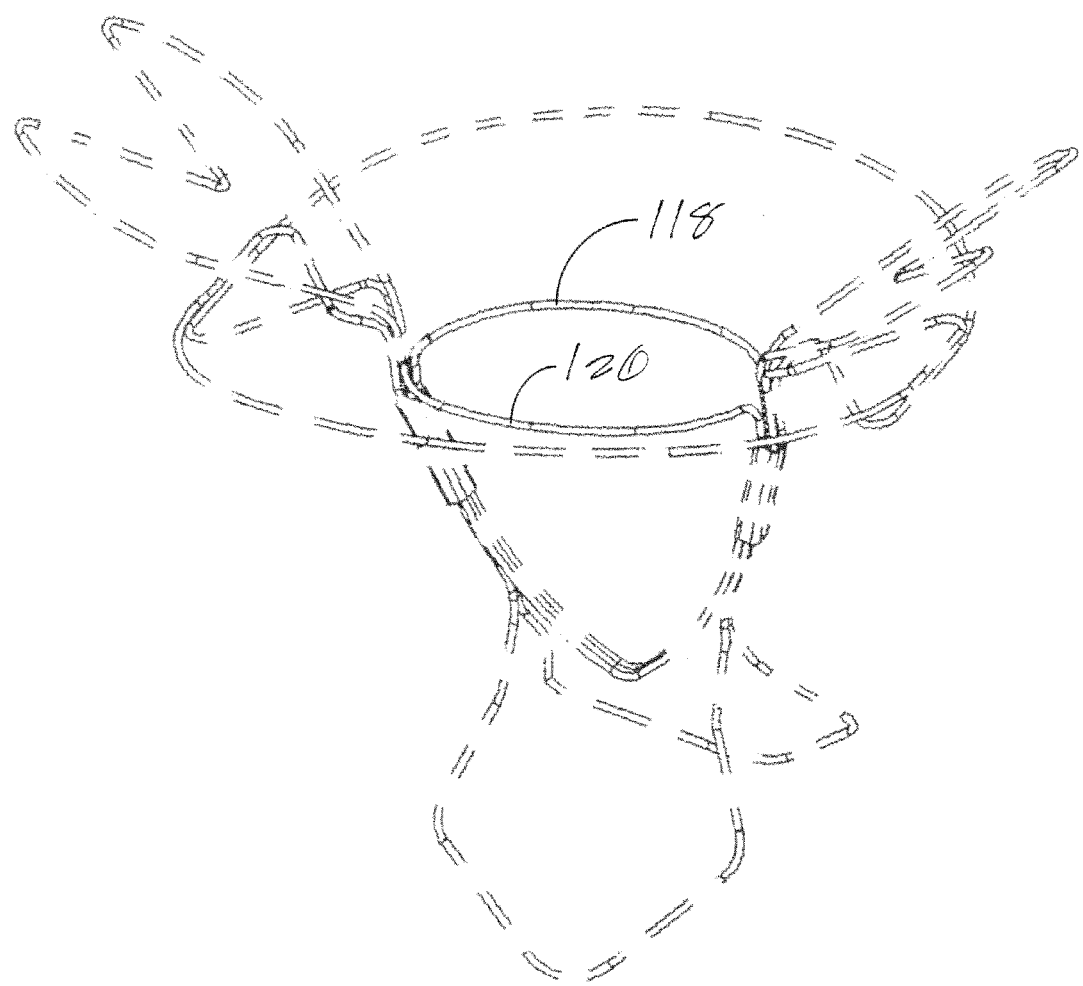
Figure 5:
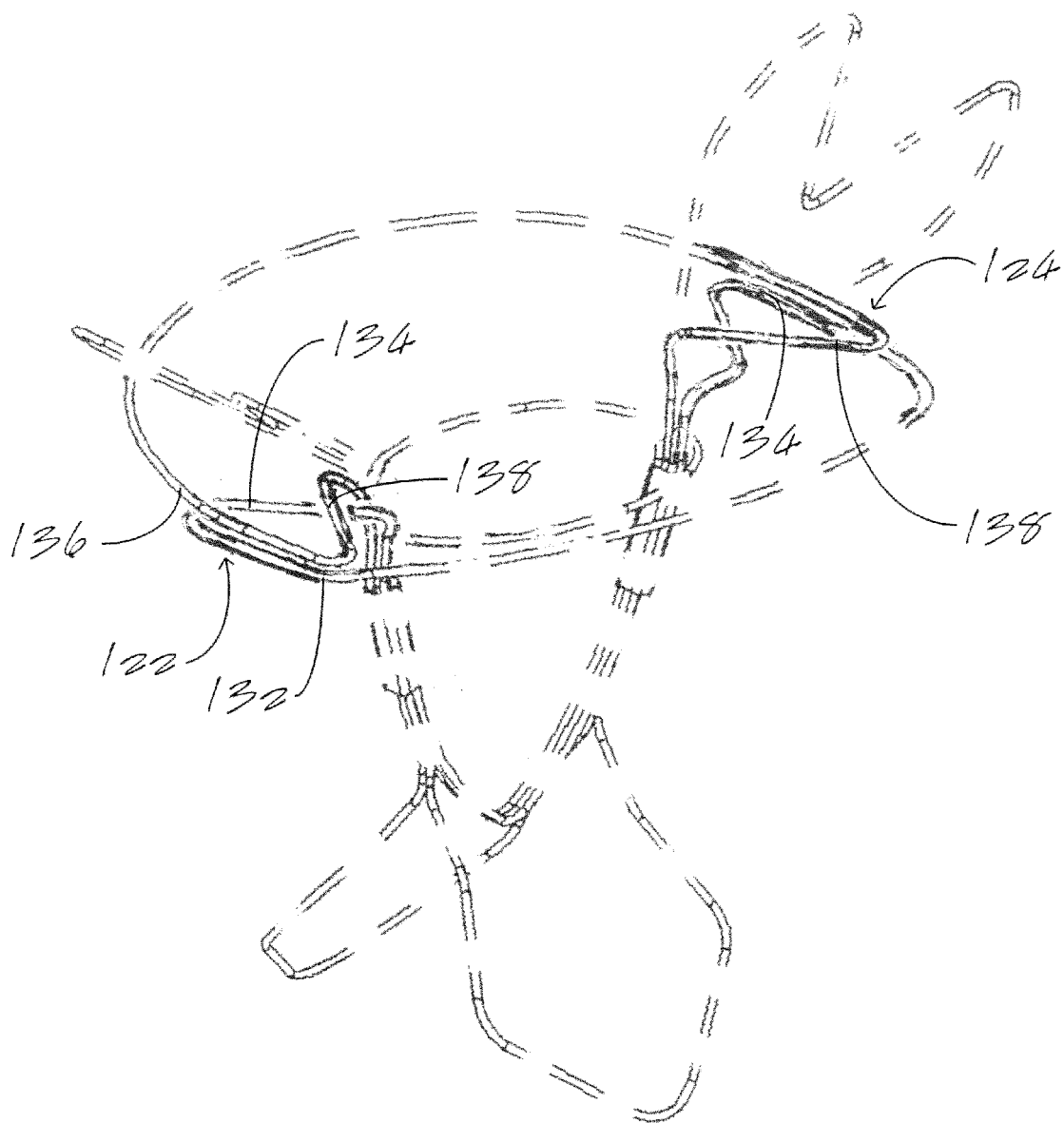
Figure 6:
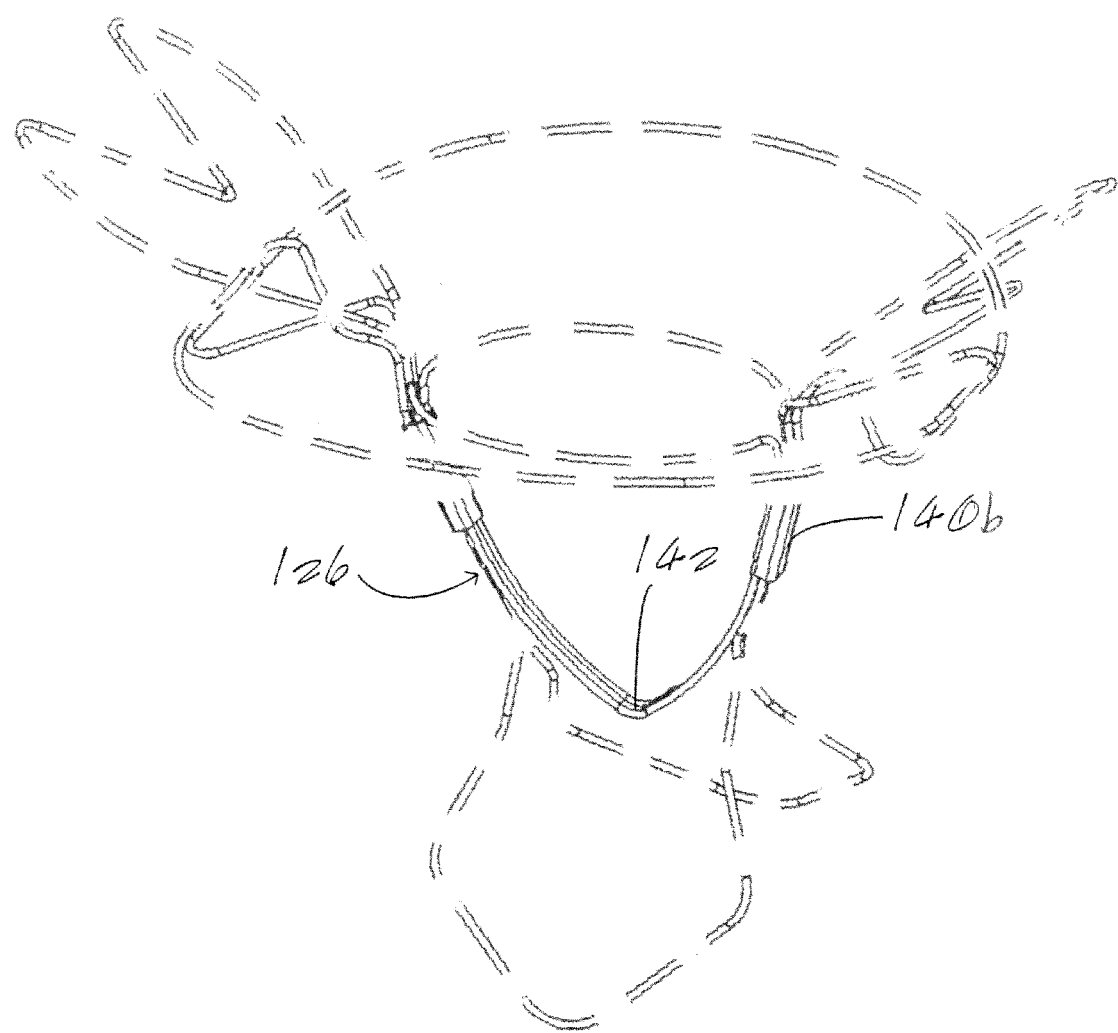
Figure 7:
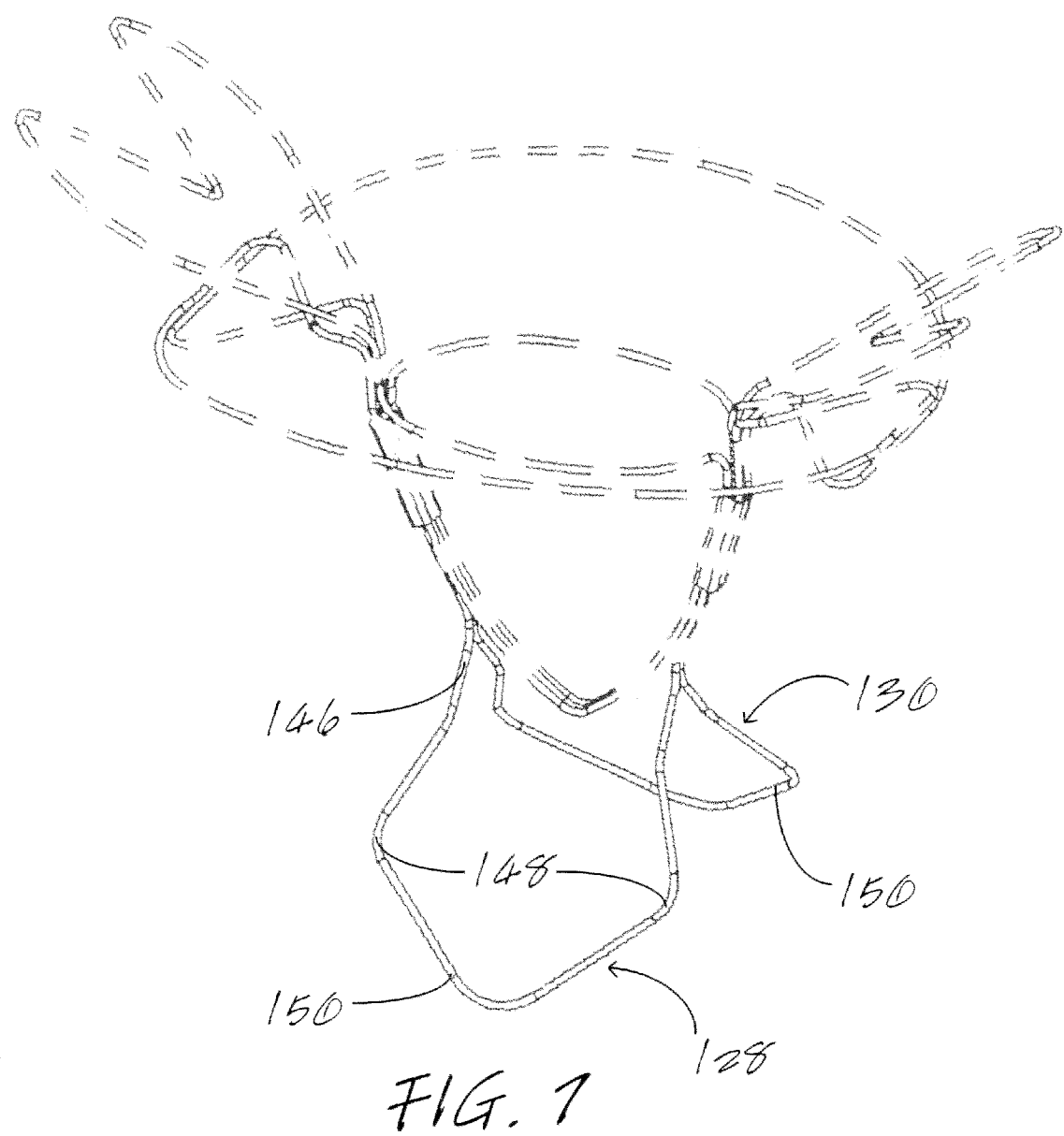

The frame 108 has a plurality of beams, as illustrated separately in FIGS. 2a, 2b and 3-7. FIGS. 2a and 2b illustrate the atrial alignment expansion beams 110 and 112. FIG. 3 illustrates the upper expansion clip beams 114 and 116. FIG. 4 illustrates the central structural beams 118 and 120. FIG. 5 illustrates the lower expansion clip beams 122 and 124. FIG. 6 illustrates the ventricular expansion curved beam 126. FIG. 7 illustrates the ventricular alignment stabilizing beams 128 and 130.

Referring to FIGS. 2a and 2b, each atrial alignment expansion beam 110 and 112 has a curved outer flange section 130a and 130b, respectively, that together defines a somewhat oval shape, which is similar to the natural shape of the atrium just above the mitral annulus. Each opposite end of the flange section 130a has a curved section 132 that transitions into an inner section 134 that extends radially towards the middle of the combined flange sections 130a, 130b. Similarly, each opposite end of the flange section 130b has a curved section 136 that transitions into an inner section 138 that extends radially towards the middle of the combined flange sections 130a, 130b. Referring also to FIG. 5, the combined sections 132+134 and 136+138 define a scissor-crossing where they overlap each other at opposite ends to form the lower expansion clip beams 122 and 124. The sections 134 and 138 transition downwardly to separate sleeves 140a and 140b (see FIG. 6), with each sleeve 140a, 140b connecting the sections 134 and 138 with the upper ends of a generally V-shaped ventricular expansion curved beam 126.

Referring to FIGS. 3 and 4, each of the upper expansion clip beams 114 and 116 resembles a butterfly wing with an M-shaped wing section 154 having wing tips 170. The two legs 160, 162 of the M shape of each wing section 154 converges downwards towards one of the sleeves 140a or 140b. Both legs 160 and 162 of each wing section 154 extend into a sleeve 140a or 140b and transition into a part of the V-shaped ventricular expansion curved beam 126. The central structural beams 118 and 120 have a central separation and transversal (i.e., in the commissure-to-commissure (C-C) direction) length that defines the extent of support to limit the upward movement, in particular the prolapsed segment of the native leaflets. This separation can be between 5 mm to 15 mm. The transversal length (in the C-C direction) is defined by allowing such natural motion to the native commissural leaflets. The atrial sections of the two membranes 180 are suspended from the central structural beams 118 and 120 to assist in limiting the prolapsed section of the native leaflets. The central structural beams 118 and 120 can also extend into the sleeves 140a, 140b and transition into a part of the V-shaped ventricular expansion curved beam 126.

The ventricular expansion curved beam 126 can actually be comprised of several layers of wire frame, but they all have a point of inflection 142 at the bottom thereof that defines the V-shape. Referring also to FIG. 7, the upper ends of the ventricular alignment stabilizing beams 128 and 130 extend from the sleeves 140a and 140b. These beams 128 and 130 resemble paddles, and each beam 128, 130 has opposing vertical sections 146 that transition into widened sections 148 before terminating at a lower V-shaped section 150 at the lowest point of each beam 128, 130.

On one embodiment, the entire frame 108 can be formed from a single wire. For example, the single wire can begin inside the sleeve 140a, extend to the sections 134, 132, 130a, 132, 134 (in that order), then through the other sleeve 140b to the beam 126 and back up through the other sleeve 140a, then on to the sections 138, 136, 130b, 136, 138 (in that order), then through the other sleeve 140b to the beam 126 and back up through the other sleeve 140a, then on to the central structural beam 118, through the other sleeve 140b to the beam 126 and back up through the other sleeve 140a, then on to the other central structural beam 120, through the other sleeve 140b to the stabilizing beam 128, then back up through the other sleeve 140a, then on to the upper expansion clip beam 114, through the same sleeve 140a to the other stabilizing beam 130, then back up through the other sleeve 140b, then on to the other upper expansion clip beam 116, and then terminating in the same sleeve 140b. In this embodiment, the ventricular expansion curved beam 126 would be formed by six passes of the single wire through each sleeve 140a and 140b.

The structure and configuration of the various beams of the frame 108 provide a number of functions and benefits:

The atrial alignment expansion beams 110 and 112 extend the frame 108 to reach and expand the C-C (commissure-to-commissure) distance of the native valve, thereby maintaining the central structural beams 118 and 120 centered in the C-C direction. The beams 110 and 112 have a cord distance larger than the C-C distance of the native valve. The beams 110 and 112 are adapted to be positioned in the left atrium (see FIGS. 9-12), and function so that the A-P (anterior-posterior) force, applied on the anterior wall, pushes the device 100 towards the native posterior leaflet. Also, these beams 110 and 112 function so that the C-C force, applied on the fibrous trigons, centers the device 100 in the C-C direction of the valve. Compression on both ends of these beams 110 and 112 tilts the curved body of these beams 110, 112 upwardly away from contact with the native valve leaflets. The plane of the beam 110, 112 is angled by 10 to 30 degrees from the horizontal plane of the frame 108. Under compression at their extremities, the beams 110, 112 deflect upwardly, keeping the beams 110, 112 from contacting the native valve leaflets and the atrium wall, and minimizing deformation of the native leaflets during the compressive state of the native valve annulus, thereby maintaining a more consistent expansion force in the C-C direction.

The central structural beams 118 and 120 provide a coaptation rest stop for the native leaflets' coaptation edges, preventing them from prolapsing into the atrium under closing pressure. The central structure defined by the beams 118 and 120 has an upward curvature to conform to the closing coaptation edge geometry of the native leaflets. This central structure does not come in contact with the commissure leaflets, preserving the native motion of the native leaflets.

Two sets of expansion clips (122+124 and 114+116) are positioned at opposite ends of this central structure to maintain this central structure aligned to the caoptation of the native leaflets by clipping in between the commissure and under the ridges of the pulmonary veins. The lower expansion clip beams 122 and 124 are formed by the overlapping of the sections 132+134 and 136+138 of the atrial alignment expansion beams 110 and 112. This overlap has a "reverse scissors motion" allowing the overlapped length to increase when the expansion beams 110 and 112 are compressed either in the C-C or A-P directions. This length increase results in the increase in the contact width of the extremities (i.e., the sections 132 and 136) of the beams 122 and 124 to the commissure area. The overlapping length increases as pressure is applied to compress the atrial alignment expansion beams 110 and 112. The tips 170 of the upper expansion clip beams 114 and 116 rest under the pulmonary vein ridges, and are symmetrical on opposite sides to each other.

The upper expansion clip beams 114 and 116 have multiple tips 170 that separate under compression on contact under the pulmonary veins ridges. As reaction forces are applied to the two ends of the atrial alignment expansion beams 110 and 112, the lower expansion clip beams 122 and 124 and upper expansion clip beams 114 and 116 separate to create a holding force between the commissure and the vein ridge. As the atrial alignment expansion beams 110 and 112 deflect upward under compression, the extremities (i.e., the sections 132 and 136) of the beams 122 and 124 apply a downward force to the commissure area. This downward force lifts the device 100 upwardly towards the atrial chamber. The amount of the upward displacement is defined by the increase in the angle of the plane of the atrial alignment expansion beams 110 and 112 relative to the horizontal plane of the central structure (i.e., 118+120). This motion further increases the pressure of the upper expansion clip beams 114 and 116 to the vein ridges. In other words, the lower expansion clip beams 122 and 124 and upper expansion clip beams 114 and 116 together function to suspend the frame assembly 102 in the C-C plane of the native valve during the complete cycle of the heart, so that the device 100 is almost "floating" in an unattached self-aligning manner in the mitral position.

The lower expansion clip beams 122 and 124 are symmetrical to each other, and rest on the commissure area. They function to maintain the height level of the central portion of the device 100 relative to the commissures.

The ventricular expansion curved beam 126 provides a secondary expansion force to the atrial alignment expansion beams 110 and 112, and functions to guide membrane support. The 'V' shape of the ventricular expansion curve beam 126 has ends connected to the ends of the central structural beams 118 and 120 to maintain the geometry of the central structural beams 118 and 120 under compressive forces applied onto the expansion beams 110 and 112. In addition, the 'V' shape of the beam 126 supports both the central structural beams 118 and 120 and the ventricular alignment stabilizing beams 128 and 130.

The ventricular alignment stabilizing beams 128 and 130 extend outwardly under the native leaflets when the device 100 is used as a mitral or tricuspid repair device. Their extremities (i.e., the sections 148 and 150) can be curved upwardly behind the native leaflets to reach under the leaflets, and to be in contact with the ventricular wall. The beam 128 or 130 that is on the side of the native posterior leaflet can extend further to be in contact under the posterior annulus. These beams 128 and 130 are located between the papillary muscles to align the frame 108 to the axis of the native valve. These beams 128 and 130 are also symmetrical to each other.

Figure 8:
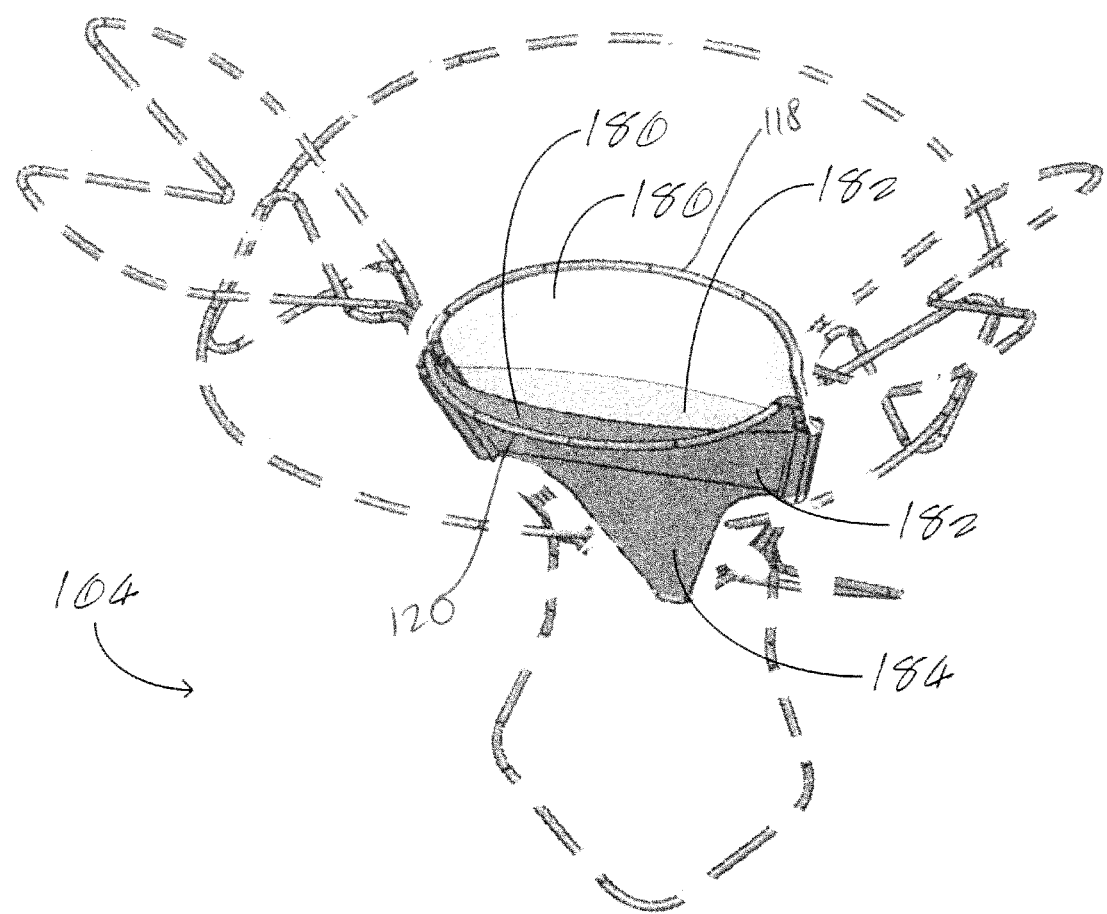
Figure 9:
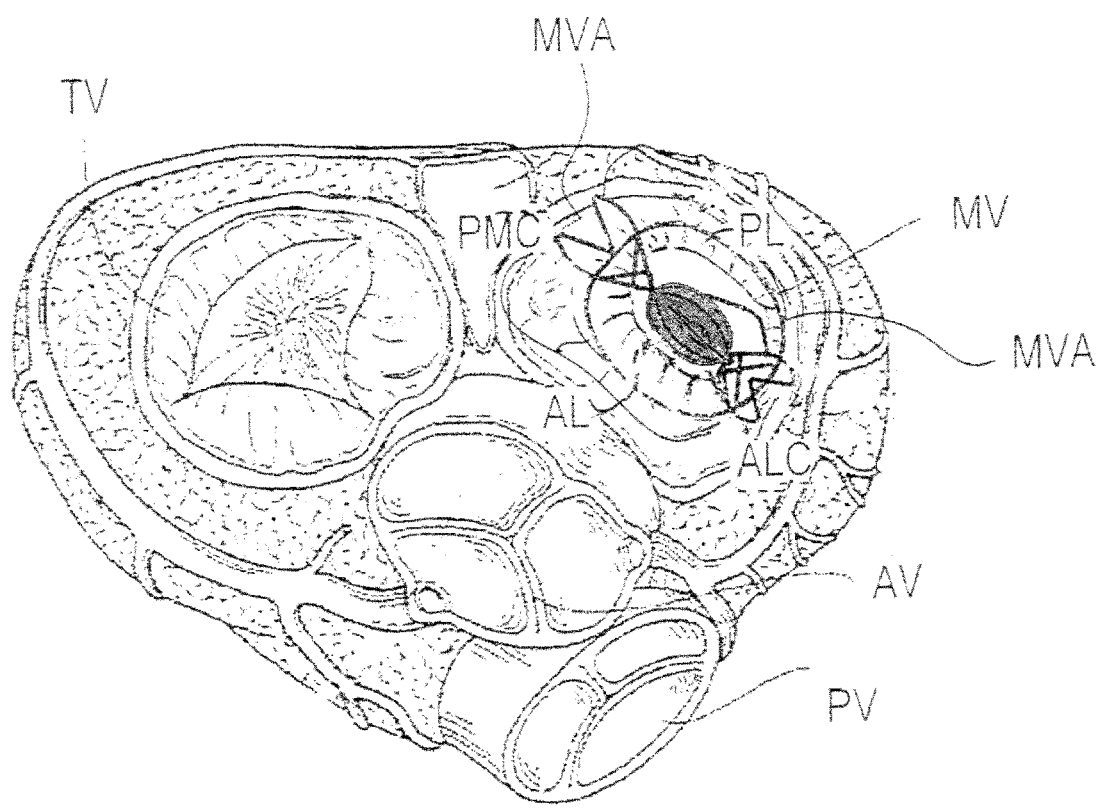
FIG. 9 a top view illustrating the cardiac valve repair device of FIG. 1a deployed in a mitral position of a human heart during diastole.
Figure 10:
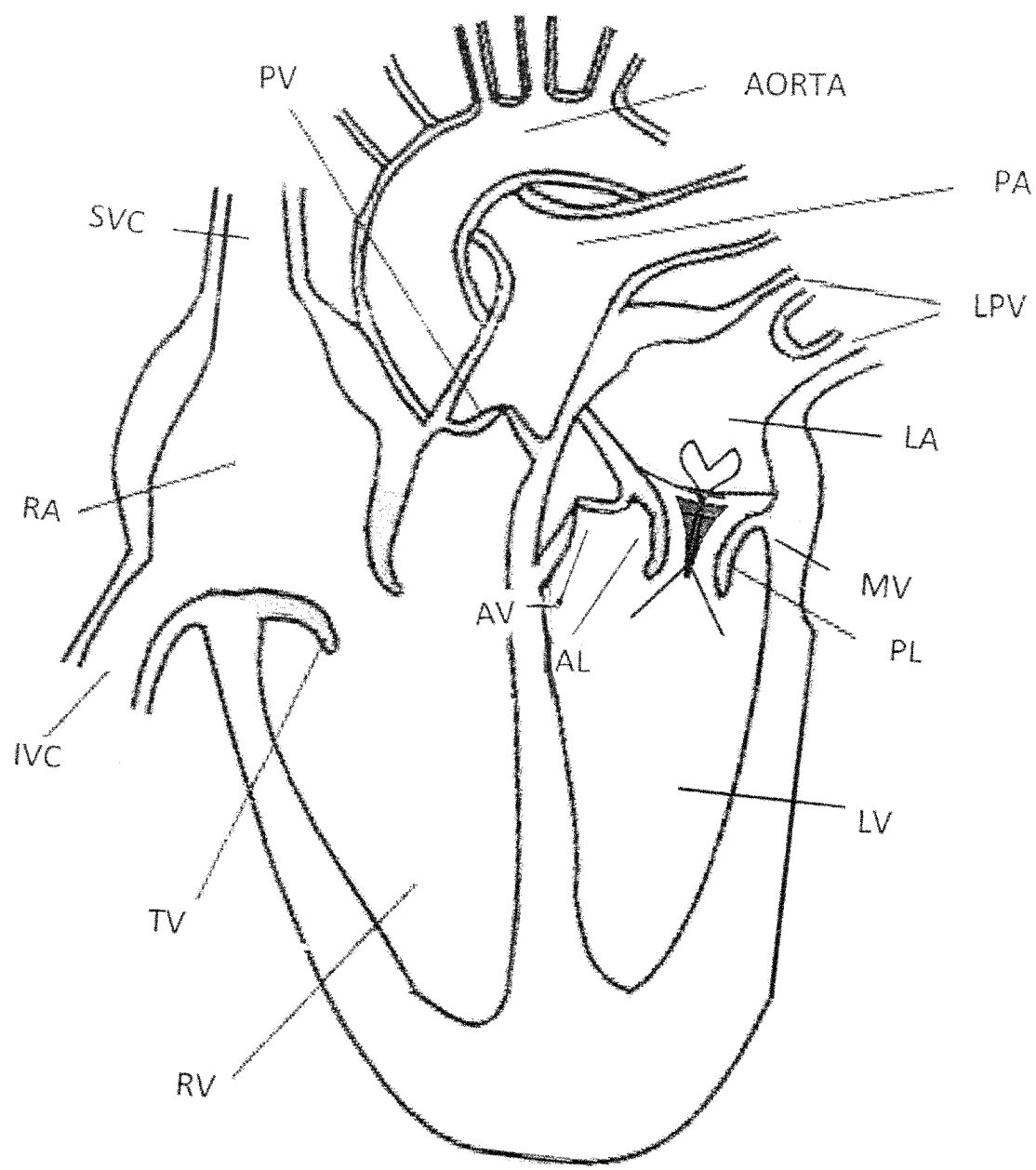
FIG. 10 a side view illustrating the cardiac valve repair device of FIG. 1a deployed in a mitral position of a human heart during diastole.
Figure 11:
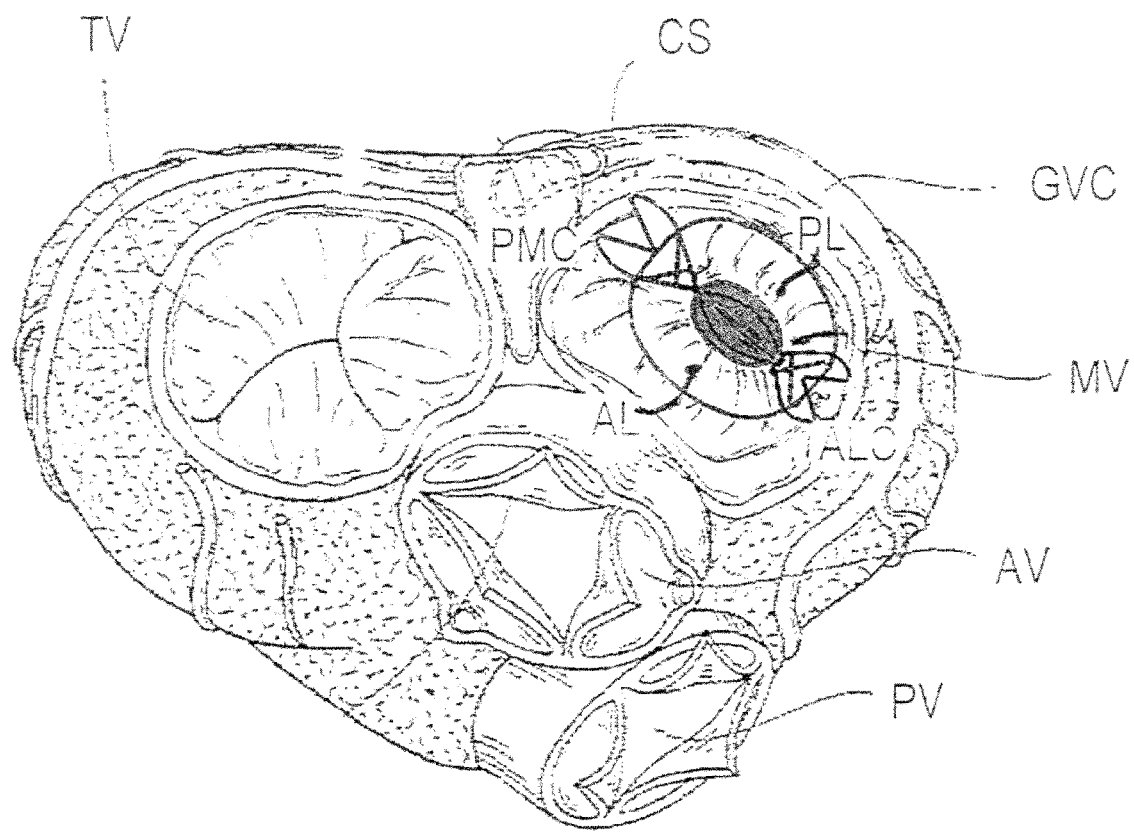
FIG. 11 a top view illustrating the cardiac valve repair device of FIG. 1a deployed in a mitral position of a human heart during systole.
Figure 12:
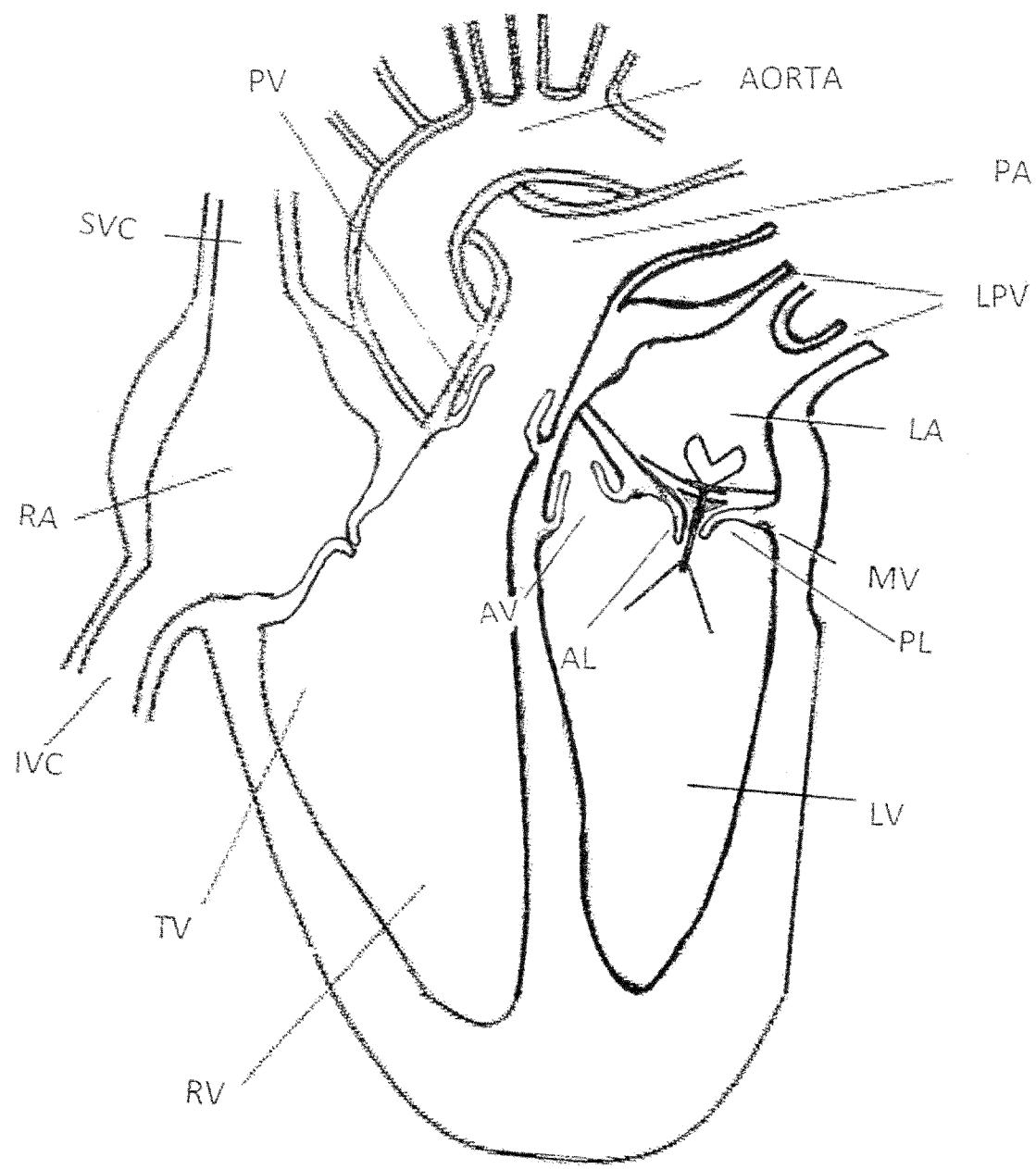
FIG. 12 a side view illustrating the cardiac valve repair device of FIG. 1a deployed in a mitral position of a human heart during systole.

Referring to FIGS. 1*a* and 8, the beams 118 and 120 of the central structure are covered with resilient biocompatible material membranes 180 to soften their contact with the closing leaflets of the native valve. These membranes 180 could be enlarged into flaps 182 forming a funnel-like shape at the center of the central structure to create a central flow maintaining the frame 108 centered along the flow pattern axis. The lower end of each flap 182 can be reduced to a separate extension strip 184 extending and attached to the nadir (apex) of the 'V' ventricular structure, thereby forming guide surfaces where the free margins of the leaflets glide upon to a stop on the central structure of the frame 108 during closure of the native valve (i.e., during systole). Each flap 18 and strip 184 combination is essentially a single piece that performs the same functions as a native leaflet.

The membranes 180 can be made of non-porous or porous mesh-like biocompatible resilient material, such as natural bovine or porcine valve tissue, or synthetic materials such as PTFE.

Referring to FIGS. 9-12, the membrane assembly 104 of the device 100 functions in the following manner. First, the following are the definitions for the abbreviations in FIGS. 9-12:

AV AORTIC VALVE
AL ANTERIOR LEAFLET
IVC INFERIOR VENA CAVA
LA LEFT ATRIUM
LV LEFT VENTRICULE
MV MITRAL VALVE
MVA MITRAL VALVE ANNULUS
PA PULMONARY ARTERY
PL POSTERIOR LEAFLET
PMC POSTERIOR MITRAL COMMISSURE
PV PULMONARY VALVE
RA RIGHT ATRIUM
RV RIGHT VENTRICULE
SVC SUPERIOR VENA CAVA
TV TRICUSPIDE VALVE

During diastole, forward flow separates the flaps 182 into its funnel shape, creating a central channel that diverts the flow of blood towards the two commissures, maintaining the orientation of the frame 108 centered along the flow axis. The native valve leaflets also expand during diastole.

During systole, the closing native leaflets push the flaps 182 inward creating guide surfaces for them to glide to their full closure resting on the central structure of the frame 108, resulting in closing of the native valve. During systole, only the extension strips 184 of the flaps 182 which extend into the ventricular chamber are subjected to ventricular pressure. Since the strips 184 are opposite and in contact to each other, the applied pressures cancel out. The flaps 182 with their lower part sandwiched between the coaptation area of the closed leaflet and with their upper portion in the atrium are subjected to atrium pressure.

When the native leaflets come to complete rest onto the central structure 118+120 during systole, the force applied on to the frame 108 to move it upwardly into the atrium is limited to only the force applied by the prolapsed section of the native leaflets coaptation, thereby minimizing the force subjected to the upper expansion clip beams 114 and 116 and the lower expansion clip beams 122 and 124.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A cardiac valve repair device, comprising a membrane assembly and a frame, the frame comprising:
   a central structure that defines a central separation;
   a pair of sleeves positioned below the central structure;
   a pair of atrial alignment expansion beams, each atrial alignment expansion beam having a curved outer flange section that together defines a generally oval shape, each opposite end of the flange section having a curved section that transitions into an inner section that extends radially towards the middle of the combined flange sections, the combined curved section and inner section of the two atrial alignment expansion beams at each opposite end defining a scissor-crossing where they overlap each other to form a separate lower expansion clip beam at each of the opposite ends thereof;

a pair of upper expansion clip beams, each having an M-shaped wing section that includes at least one wing tip, each wing section having two legs that converge downwards towards one of the sleeves, with one leg transitioning to a part of a central structure a V-shaped ventricular expansion curved beam extending below the two sleeves, with the membrane assembly secured to the V-shaped ventricular expansion curved beam; and a pair of ventricular alignment stabilizing beams extending downwardly from the two sleeves.

2. The device of claim 1, wherein each ventricular alignment stabilizing beam has opposing vertical sections that transition into widened sections before terminating at a lower V-shaped section.

3. The device of claim 1, wherein the central structure comprises a pair of central structural beams having a separation between 5 mm and 15 mm.

4. The device of claim 1, wherein a clipping space is defined between each pair of upper expansion clip beams and lower expansion clip beams on opposite ends of the central structure.

5. The device of claim 1, wherein the frame is made from a single wire.

6. The device of claim 1, wherein the V-shaped ventricular expansion curved beam is formed of a plurality of wires.

* * * * *